(12) United States Patent
Jones et al.

(10) Patent No.: US 7,455,403 B2
(45) Date of Patent: Nov. 25, 2008

(54) SIMULTANEOUS VISION EMULATION FOR FITTING OF CORRECTIVE MULTIFOCAL CONTACT LENSES

(75) Inventors: Larry G. Jones, Jacksonville, FL (US); John R. Buch, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 288 days.

(21) Appl. No.: 11/463,053

(22) Filed: Aug. 8, 2006

(65) Prior Publication Data
US 2006/0285074 A1    Dec. 21, 2006

Related U.S. Application Data

(62) Division of application No. 10/609,699, filed on Jun. 30, 2003, now Pat. No. 7,131,727.

(51) Int. Cl.
*G02C 7/04* (2006.01)
*A61B 3/10* (2006.01)

(52) U.S. Cl. .................... 351/161; 351/228; 351/160

(58) Field of Classification Search ............. 351/160, 351/161, 168, 228, 229, 230, 246, 247
See application file for complete search history.

(56) References Cited

U.S. PATENT DOCUMENTS

| | | | | | |
|---|---|---|---|---|---|
| 3,290,924 | A | * | 12/1966 | Heinrich et al. | 73/61.76 |
| 3,891,311 | A | * | 6/1975 | Fletcher et al. | 351/245 |
| 4,798,457 | A | * | 1/1989 | Morohashi et al. | 351/235 |
| 5,376,086 | A | * | 12/1994 | Khoobehi et al. | 606/4 |
| 5,450,145 | A | * | 9/1995 | Valentine | 351/243 |

* cited by examiner

*Primary Examiner*—Nini Legesse (57) ABSTRACT

An emulator including a beam splitter for splitting incoming light energy into a first component directed along a first optical path, and a second component directed along a second optical path distinct from the first optical path. The emulator includes a first receptacle positioned to pass light energy directed along only the first optical path. The first receptacle is capable of receiving an add lens for providing an add power. A beam combiner is positioned to combine light energy of the second component with light energy of the first component that has passed the first receptacle, i.e. to have the add power applied, and to direct the combined light energy along a common optical path. Additional receptacles are provided that are capable of receiving a sphere and/or a cylindrical lens in position to pass the combined light energy traveling along the common optical path.

24 Claims, 12 Drawing Sheets

SIMULTANEOUS VISION EMULATION FOR FITTING OF CORRECTIVE MULTIFOCAL CONTACT LENSES

FIELD OF THE INVENTION

The present invention relates generally to corrective lenses for enhancing visual acuity, and more particularly to methods and devices for fitting of corrective multifocal contact lenses. The application is a divisional of U.S. application Ser. No. 10/609,699 filed Jun. 30, 2003 now U.S. Pat. No. 7,131,727.

DISCUSSION OF RELATED ART

Current popular clinical methodology for fitting a person with corrective lenses involves development of a vision prescription using a phoropter. Typically, an optometrist or other health care professional has the person (patient) look through the phoropter to view a chart displayed at a distance. The health care professional then uses the phoropter to introduce into the person's sight path various lenses, or combinations of lenses, to determine the optimal add, sphere and/or cylinder parameters of a corrective lens prescription for the person. This typically involves having asking the person compare the visual acuity from various combinations of lenses and report which combination provides the clearest appearance of text on the chart. Custom fitted eyewear can then be manufactured for the person according to the prescription thus obtained.

This approach is suitable for single vision and monovision eyeglasses or contact lenses. This approach is also suitable for bifocal/multifocal eyeglasses as a person can manipulate his/her eye/pupil to selectively focus on an object through different parts of a bifocal/multifocal eyeglass lens having areas characterized by different focal lengths. This approach, however, has proven inadequate for bifocal/multifocal contact lenses because such contact lenses have a principle of operation different from that of the corrective eyewear mentioned above.

In particular, most soft multifocal contact lenses operate on a principle of "simultaneous vision." Like multifocal eyeglasses, multifocal contact lenses have different areas which have different focal lengths, one optical power for distance vision and the other for near vision. Accordingly, the focal power varies over the areas of the multifocal contact lens. Unlike multifocal eyeglasses, however, both of these areas of different focal lengths in multifocal contact lenses are positioned on a wearer's eye over the pupil and thus the wearer cannot electively focus through different parts of the lens. Instead, multiple images of various degrees of sharpness, corresponding to the focal power/length of each area of the lens, are focused simultaneously on the retina of the wearer's eye (the "simultaneous vision effect"). It is believed that the human brain separates, combines or otherwise processes these images so that the individual perceives a single, satisfactorily clear image.

Phoropters cannot emulate this simultaneous vision effect and thus are not suitable or optimal for multifocal contact lenses. As a result, a person is usually fitted with multifocal contact lenses by first obtaining a vision prescription using a phoropter, dispensing multifocal contact lenses meeting that prescription, then testing the person's vision while wearing those multifocal contact lenses. Typically, the person reports less than optimal visual acuity, and a trial-and-error approach follows in which the person is fitted with additional sets of multifocal contact lenses until satisfactory visual acuity is reported. This iterative process is frustrating and time consuming as it typically takes 15-45 minutes for each set of contact lenses to properly center on the eyes, to become suitably wet, and to otherwise settle before testing for visual acuity. This lengthy process is costly for health care professionals, and such costs are compounded by the need to discard one or more sets of rejected multifocal contact lenses.

SUMMARY

The present invention provides an emulator that can be used during fitting of a person for multifocal contact lenses to emulate a multifocal contact lens by producing a simultaneous vision effect on a retina of an eye. An emulator device in accordance with the present invention includes a beam splitter positioned to split incoming light energy into a first component directed along a first optical path, and a second component directed along a second optical path distinct from the first optical path. The device further includes a first receptacle positioned to pass light energy directed along only the first optical path. The first receptacle is capable of receiving an add lens for providing an add power. A beam combiner is positioned to combine light energy of the second component with light energy of the first component that has passed the first receptacle, i.e. to have the add power applied, and to direct the combined light energy along a common optical path. Second and third receptacles are provided which are capable of receiving a sphere lens and/or a cylindrical lens. These receptacles are provided in position to pass the combined light energy traveling along the common optical path.

In this manner, the emulator disperses incoming light energy along two distinct paths, applies an add power to one of the paths, and a sphere and/or cylindrical power to combined light energy from the two distinct paths. This creates a near image, i.e. an image that is in focus at a relatively near position, and a distance image, i.e. an image that is in focus at a relatively distant position. Both images are simultaneously focused on a retina of an eye of a person looking through the emulator, thereby creating a simultaneous vision effect comparable to that created by a multifocal contact lens.

The emulator device may include two oculars, each ocular including the optics discussed above. The device may further include an interpupillary distance mechanism for adjusting a distance between the ocular for alignment with variously spaced pupils, and a convergence mechanism capable of rotating the oculars to cause sight/optical paths therethrough to converge at a near point. This simulates a reading condition in which the human eyes pivot inwardly to focus at a point relatively near the face.

A method for emulating a multifocal contact lens to produce a simultaneous vision effect on a retina of an eye is also provided.

BRIEF DESCRIPTION OF THE DRAWINGS

The present invention will now be described by way of example with reference to the following drawings in which.

DETAILED DESCRIPTION

The present invention provides a device and method that can be used during fitting of a patient for multifocal contact lenses to emulate a multifocal contact lens by producing a simultaneous vision effect on a retina of an eye. In this manner, the inaccuracies relating to development of a prescription using a phoropter, which does not operate on a simultaneous vision principle, and the resulting waste of time and money for trial-and-error based prescription tuning can be eliminated. Accordingly, an accurate multifocal contact lens prescription may be obtained without the need to place any contact lenses on the eyes.

Figure 1:
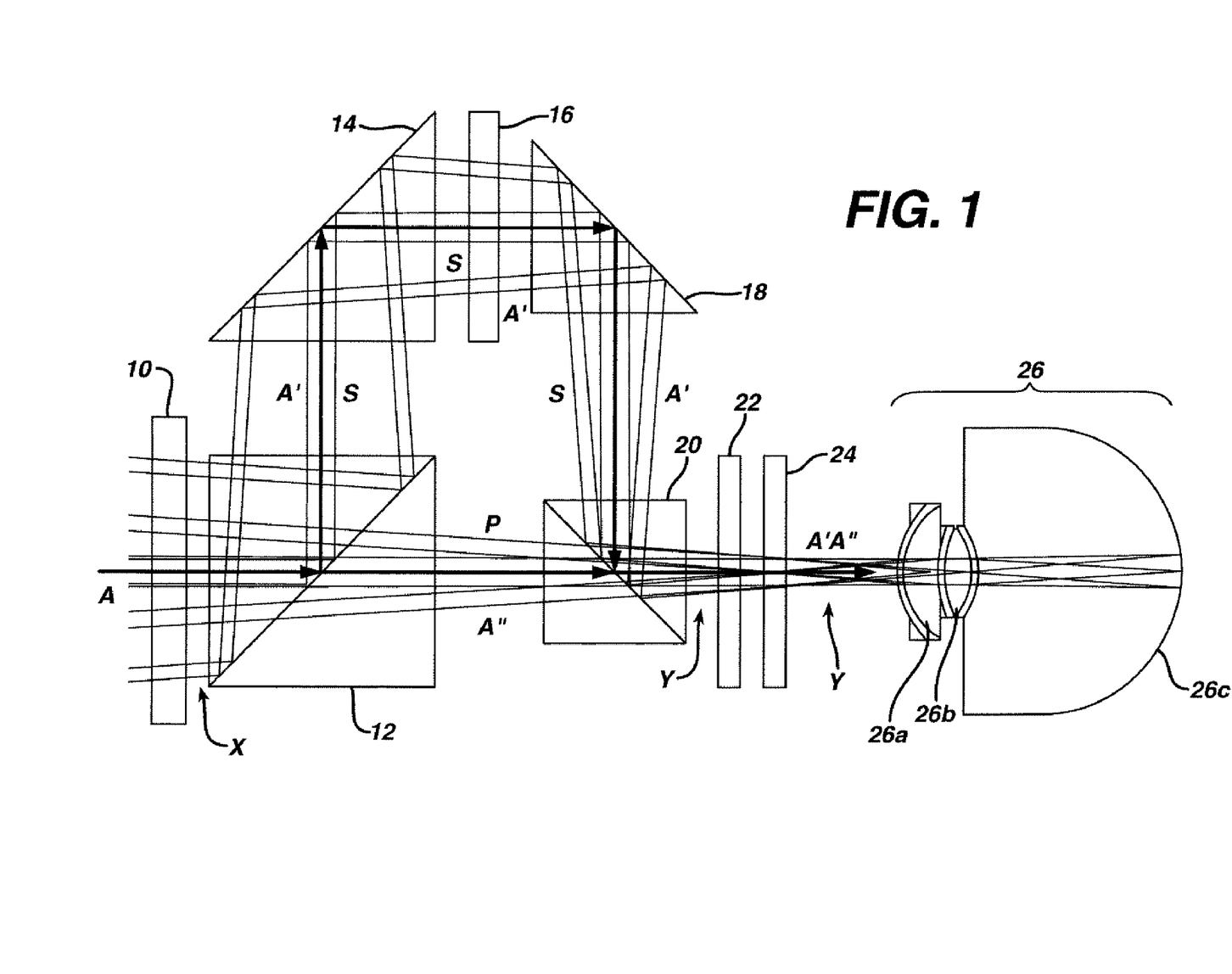
FIG. 1 is a schematic diagram of a simultaneous vision emulator in accordance with the present invention.

Referring now to FIG. 1, a schematic diagram illustrates how incoming light energy is manipulated to emulate simultaneous vision in accordance with the present invention. Such incoming light energy may be ambient lighting in an optometrist's office, such as that reflected from a conventional eye chart viewed by a person during the eye examination procedure. Such light energy is typically non-polarized polarized, as shown at A in FIG. 1. It will be appreciated that FIG. 1 includes a ray trace model for illustrative purposes.

In this example, though optional, such incoming light energy A is first passed through a polarizer 10, e.g. an absorption polarizer, which receives incoming non-polarized or randomly polarized light and provides an output of linearly polarized light oriented at an angle relative to a reference plane. The linearly polarized light travels an optical path X into a beam splitter 12. The beam splitter 12 is positioned to split incoming light energy into a first component A' having a first polarization (the "S" polarization), and a second component A" having a second polarization (the "P" polarization). It should be noted that a 50%/50% ratio between the two polarizations is assumed with randomly polarized scene lighting. The absorption polarizer 10 can be used to ensure a 50%/50% ratio by mounting the polarizer at 45 degrees relative to a reference plane/the beam splitter 12. This ratio is presently believed to be advantageous. Alternatively, the polarizer can be oriented at other angular orientations to tune the intensity ratio between the S and P polarized components exiting the beam splitter 12. Optionally, a cube polarizer or similar component may be used instead of the absorption polarizer 10.

The beam splitter 12 directs the first and second components along two distinct optical paths, namely, an S path for near vision, and a P path for distance vision. By way of example, the beam splitter 12 may be a visible waveband cube splitter, or a visible waveband cube polarizer. Such optical components are well known in the art. It should be noted, however, that use of the cube splitter tends to transmit some light energy that would otherwise be reflected with a cube polarizer, thereby resulting in a dimmer appearance of a viewed image.

In accordance with the present invention, one of the components is passed through an add lens. In the example of FIG. 1, the first component A' is passed through add lens 16, which is positioned to pass light energy traveling the S path.

The add lens 16, in cooperation with the sphere lens 22 discussed below, focuses the first component's light energy for near viewing. This add lens may be selectively interchanged until the person reports satisfactory visual acuity, as discussed further below. The second component A" is not passed through the add lens.

The first component A', as refracted by the add lens 16, and the second component A" are then directed into a beam combiner 20 positioned to combine the first and second components A', A" and direct them along a common optical path Y. By way of example, the beam combiner 20 may be a visible waveband cube splitter, or a visible waveband cube polarizer, as discussed above with respect to the beam splitter 12. The beam splitter 12 and beam combiner 20 need to be properly oriented to achieve the desired effect described above, as will be appreciated by those skilled in the art.

In the example of FIG. 1, reflectors 14,18, such as total internal reflection (TIR) fold prisms 14,18 functioning in TIR mode, are positioned to direct the first component A' of the light energy from the beam splitter 12, through the add lens 16, and to the beam combiner 20, as shown in FIG. 1. Accordingly, the reflectors 14, 18 help to define the S path. This provides for physical separation of the first and second components A', A" to allow space for insertion of an add lens in the optical path (S path) of the first component A' and without interfering with the optical path (P path) of the second component A". Alternatively, a front surface or rear surface mirror could be used as reflectors 14,18 in place of the prisms to direct the first component A' along an S path in a similar manner.

The combined light energy A'A" exiting the beam combiner 20 travels a common path and then passes through a sphere lens 22 and/or a cylindrical lens 24 of the emulator before it enters the person's cornea 26a and lens 26b and is projected onto the retina 26c of the human eye 26. The sphere lens 22 focuses the combined light energy for distance vision. The cylinder lens corrects for astigmatism. The sphere and cylindrical lenses 22, 24 may be selectively interchanged until the person reports satisfactory visual acuity, as discussed further below. Accordingly, when a person views the typical eye chart through the emulator, a near image (from the S path) and a distance image (from the P path) are simultaneously presented on the person's retina 26c to provide the simultaneous vision effect. Accordingly, a vision prescription obtained using the add, sphere and/or cylinder parameters of the add, sphere and/or cylindrical lenses 16, 22, 24 providing satisfactory visual acuity will be accurate for use to prescribe multifocal contact lenses, negating the need for trial-and-error testing.

Preferably, a device for emulating simultaneous vision includes two sets of the optical components discussed above with respect to FIG. 1, namely, one set for each eye. Each set is referred to herein as an ocular. In this manner, if desired, both eyes may be used in viewing the chart and developing a vision prescription. Accordingly, the device is a stereoscopic emulation device. It should be noted that an occluding lens may be inserted in one ocular to allow viewing with only one eye, even when the device includes two oculars.

Figure 2A:
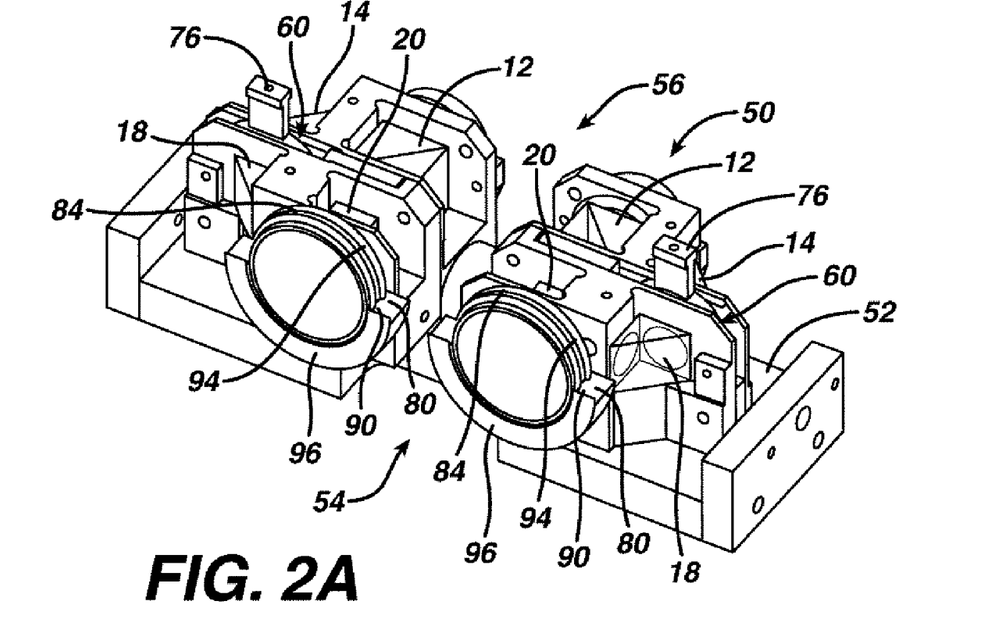
FIGS. 2A and 2B are front and rear perspective views of an exemplary simultaneous vision emulator device in accordance with the present invention.
Figure 2B:
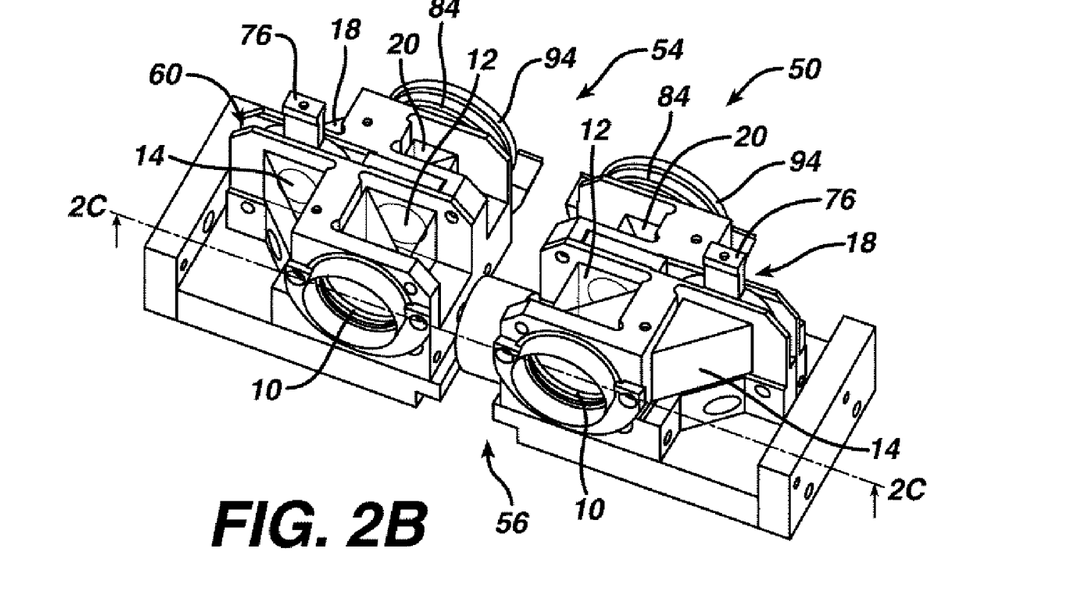
Figure 2C:
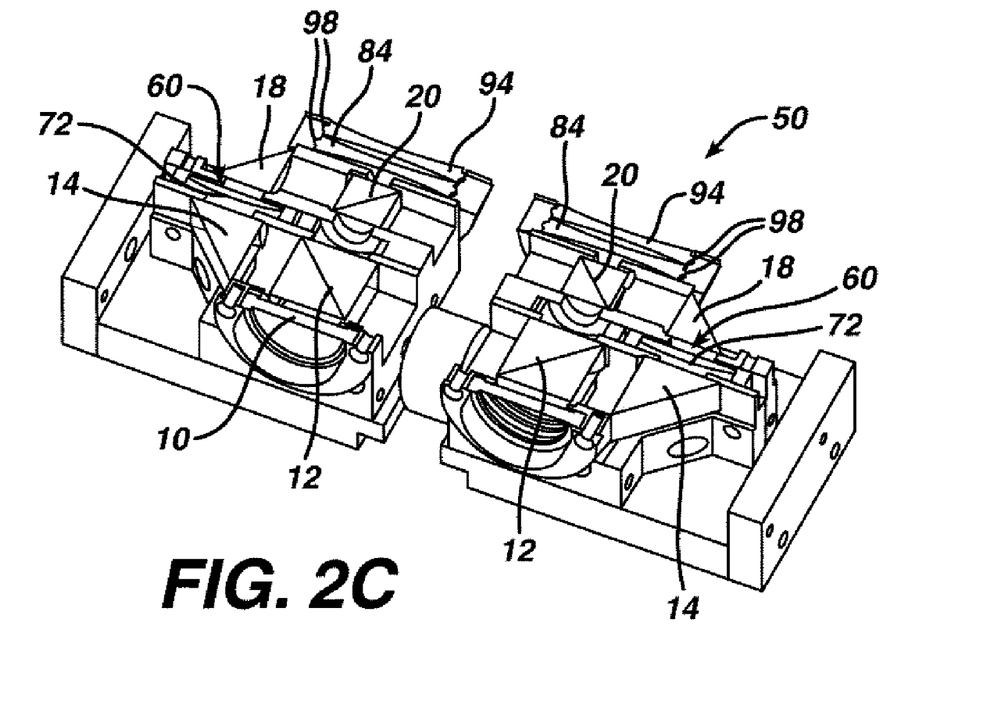
FIG. 2C is a cross-sectional perspective view of the device of FIG. 2B, taken along line 2C-2C of FIG. 2B.

FIGS. 2A, 2B and 2C are front, rear and cross-sectional perspective views of an exemplary simultaneous vision emulator device 50 in accordance with the present invention. This emulator device 50 includes two oculars, each having optics discussed above with reference to FIG. 1. As shown in FIGS. 2A-2C, the device 50 includes a housing 52 having front 54 and rear 56 ends. For illustrative purposes, a portion of the housing 52 is shown removed in FIGS. 2A-2C. Referring now to FIGS. 1 and 2A-2C, the housing 52 supports a polarizer 10, e.g. an absorption polarizer, for linearly polarizing incoming light energy, as discussed above with reference to FIG. 1. In the example of FIGS. 2A-2C, the absorption polarizer 10 is fixedly mounted at a 45 degree angle with respect to the beam splitter 12 to ensure an equal distribution of incoming randomly polarized light energy into first and second components having first and second polarizations. Alternatively, the polarizer 10 can be fixedly mounted at an alternative angle with respect to the beam splitter to provide an alternative intensity ratio. As another alternative, the polarizer 10 can be rotatably mounted with respect to the beam splitter 12 to be selectively adjustable by a user of the emulator 50 to vary the intensity ratio between the first and second components A', A".

Light energy entering each polarizer 10 travels a path similar to that shown in FIG. 1 as a result of the arrangement of the beam splitters 12, reflective mirrors/prisms 14,18, and beam combiners 20, which are optically aligned to define respective optical paths thereamong, the optical paths being similar to those shown in FIG. 1.

In the exemplary embodiment of FIGS. 2A-2C, the emulator 50 includes first receptacles positioned to pass light energy directed along one of the optical paths, i.e. the near vision (S) optical path traveled by the first component A', as illustrated in FIG. 1. Each first receptacle is capable of receiving an add lens shown in block form at 16 in FIG. 1. In the embodiment of FIGS. 2A-2C, the receptacle is provided as a slot 60 in the housing 52 for receiving a lens insert functioning as the add lens 16 of FIG. 1.

Figure 3:
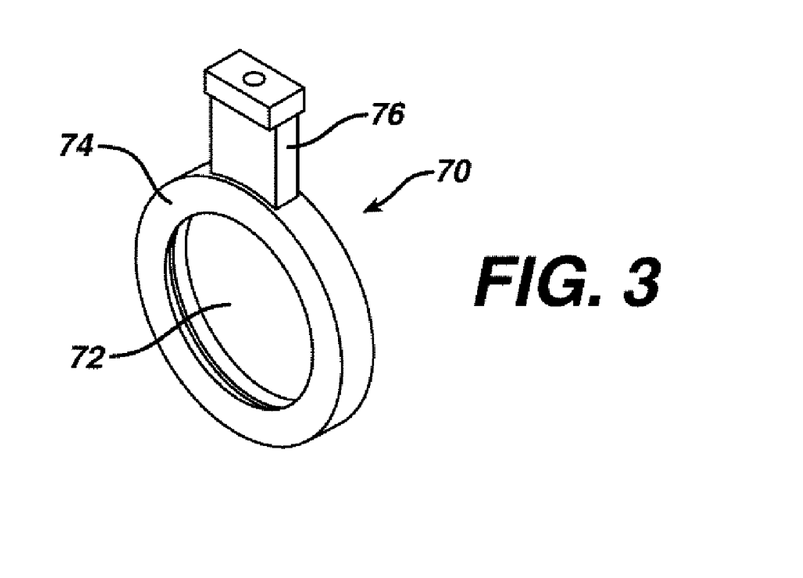
FIG. 3 is a perspective view of an exemplary lens for use with the device of FIGS. 2A-2C.

An exemplary lens insert 70 is shown in FIG. 3. This exemplary lens insert 70 includes an optical lens 72 providing an add power, a frame 74 securing the lens 72, and a handle 76 extending from the frame 74 to facilitate manual grasping of the lens insert 70 for insertion in and removal from the slots 60 of the emulator 50. It will be appreciated that a set of lens inserts are provided, each having optical lenses of a different add power, such that the lens inserts 70 may be used interchangeably to apply the desired add power to a viewer's sight path. The slots 60 and lens inserts 70 are configured such that the respective optical lens 72 is optically aligned with light energy traveling the near vision (S) optical path when the lens insert 70 is properly seated in the slot 60.

In the exemplary embodiment of FIGS. 2A-2C, each ocular of the emulator 50 also includes a second receptacle 80 positioned to pass combined light energy traveling along the common optical path Y. Each second receptacle 80 is capable of receiving a sphere lens 84 in optical alignment with light energy traveling the common path. A set of interchangeable sphere lenses are provided so that a selected sphere lens may be inserted into a selected second receptacle 80 to apply a desired sphere power to a viewer's sight path.

Each ocular of the exemplary emulator 50 also includes a third receptacle 90 provided in position to pass combined light energy traveling along the common optical path Y. Each third receptacle 90 is capable of receiving a cylindrical lens 94 in optical alignment with light energy traveling the common path. A plurality of interchangeable cylindrical lenses are provided so that a selected cylindrical lens may be inserted into a selected third receptacle 90 to apply a desired cylindrical power to a viewer's sight path, e.g. to corrected for astigmatism. In a preferred embodiment, each second receptacle 80 is positioned between a respective beam combiner 20 and a respective third receptacle 90, as shown in FIGS. 2A-2C.

The second receptacle 80 is provided to receive a lens functioning as the sphere lens 22 of FIG. 1. The third receptacle 90 is provided to receive a lens functioning as the cylindrical lens 24 of FIG. 1. In the exemplary embodiment of FIGS. 2A-2C, each of the second and third receptacles 80, 90 is provided as a respective drop lens holder 96, which includes a respective groove 98 for holding a lens, as best shown in FIGS. 4B and 4C.

Accordingly, a person seeking corrective multifocal contact lenses may be asked by a health care professional to position his eyes adjacent the front end 54 of the emulator 50, and to look through the emulator's oculars at a vision chart. The health care provider may repeatedly interchange add, sphere and/or cylindrical lenses of each ocular and ask the person to compare visual acuity until an optimal combination of lenses, and thereby a vision prescription, is obtained.

Figure 4A:
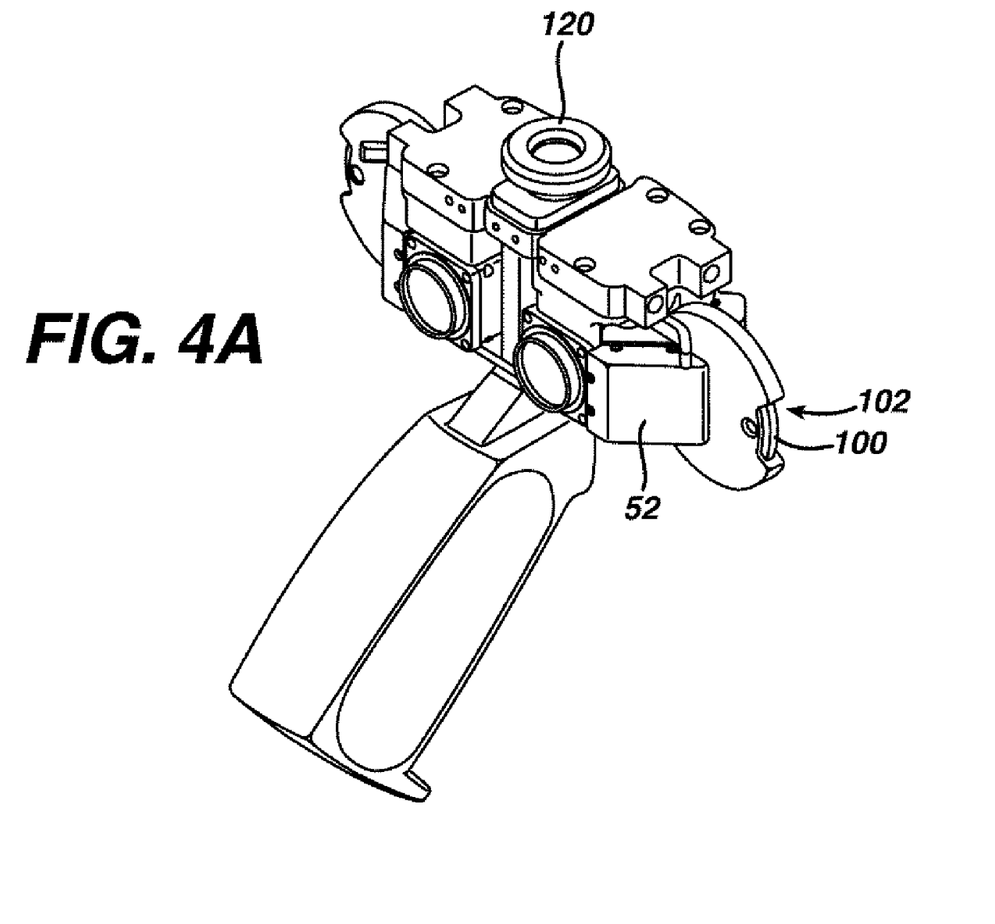
FIGS. 4A and 4B are rear and front perspective views of an alternative embodiment of the device of FIGS. 2A-2C.
Figure 4B:
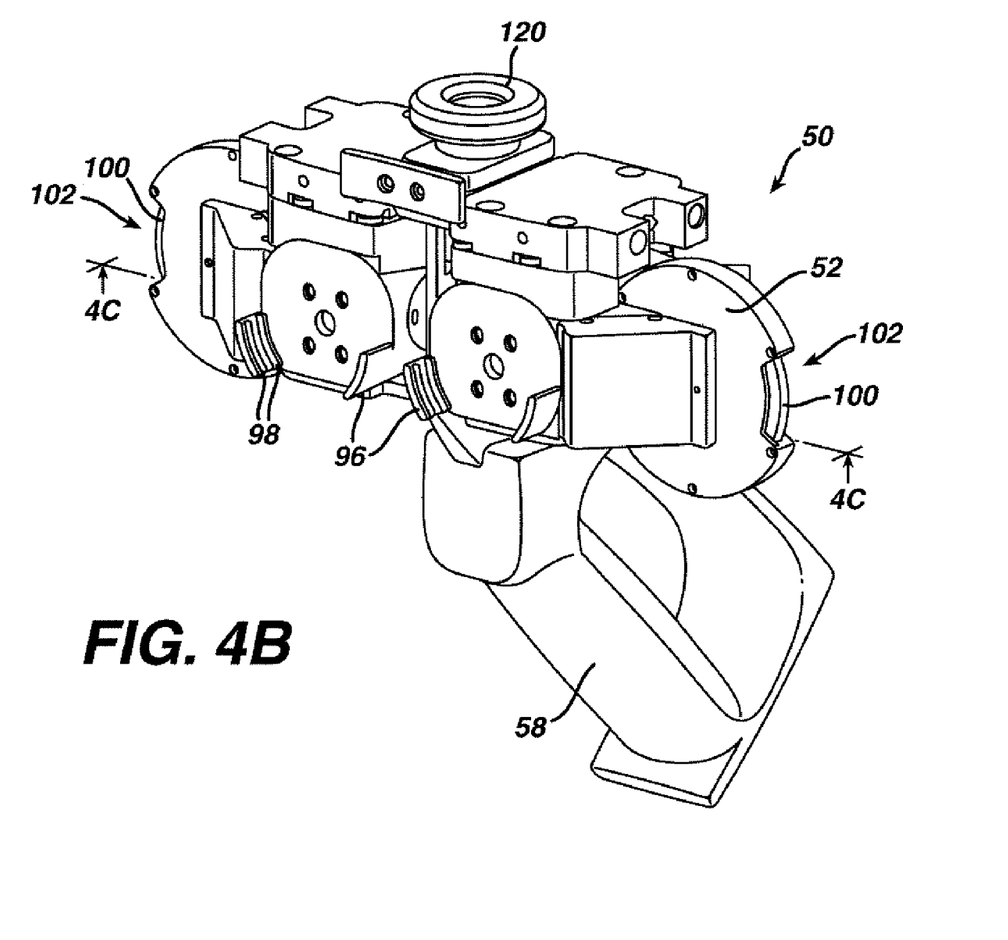
Figure 4C:
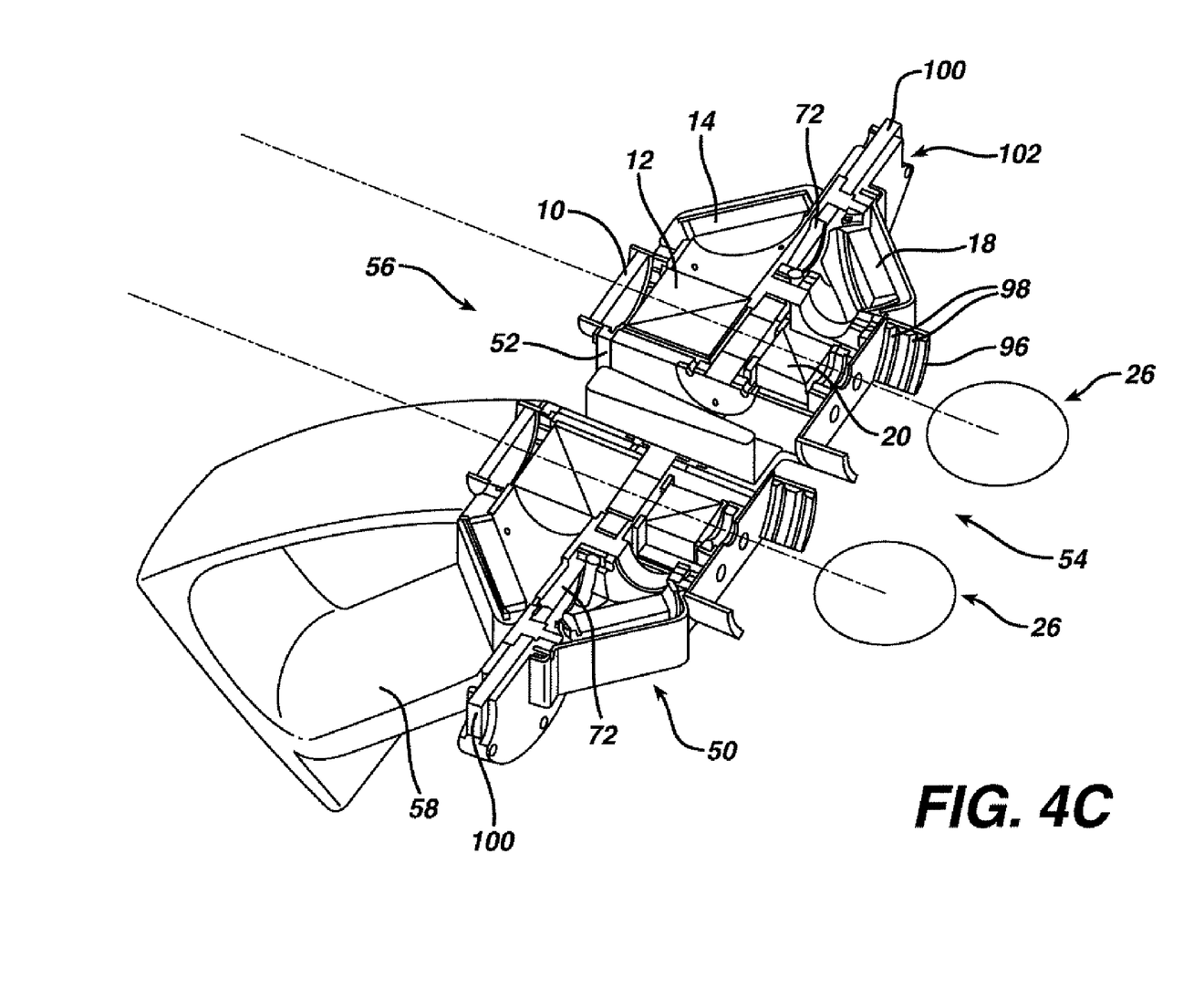
FIG. 4C is a cross-sectional perspective view of the device of FIGS. 4A and 4B, taken along line 4C-4C of FIG. 4B.

FIGS. 4A-4C are rear, front and cross-sectional perspective views of an alternative embodiment of the emulator device 50 of FIGS. 2A-2C. The oculars of the exemplary emulator 50 of FIGS. 4A-4C are very similar to those of FIGS. 2A-2C, as best shown in FIG. 4C. However, the housing 52 of this exemplary emulator 50 includes a handle 58 so that the person or health care professional may easily hold the emulator 50 adjacent the person's face during development of a vision prescription. Alternatively, the emulator 50 may be configured, e.g. with a mounting bolt, for mounting atop a tripod, etc. In addition, each ocular of this exemplary emulator 50 includes a wheel 100 capable of supporting several add lenses 72. Each add lens provides a respective add power. Each wheel 100 is rotatably mounted relative to the beam splitter 12 and/or housing 50 for selective positioning of an add lens in the area of the first receptacle 60 such that the light energy of the first component traveling the S optical path will pass through the selected add lens 72. Such wheels are generally well known in the art of optometry equipment, such as phoropters. Accordingly, a health care professional can interchange add lenses positioned in the optical path by rotating the wheel 100 to apply an add lens of the desired power to the person's sight path. This may be achieved by manually rotating the wheel 100 as it is exposed through an aperture 102 in the housing 50. A ball or other type detent mechanism may be provided to facilitate the alignment of the lenses with the optical path. Various suitable detent mechanisms are well known in the art.

The exemplary device of FIGS. 4A-4C also includes an interpupillary distance (IPD) mechanism capable of varying the distance between the oculars of the emulator 50, e.g. between the second and/or third receptacle 80, 90. In other words, the IPD mechanism allows for manipulation of the left eye and right eye oculars of the emulator to align the common paths exiting the emulator 50 with the pupils of the person having his vision tested. This is necessary because interpupillary distance varies among individuals. Various IPD mechanisms are generally known in the art for optometry equipment, and any suitable IPD mechanism may be used.

Figure 6:
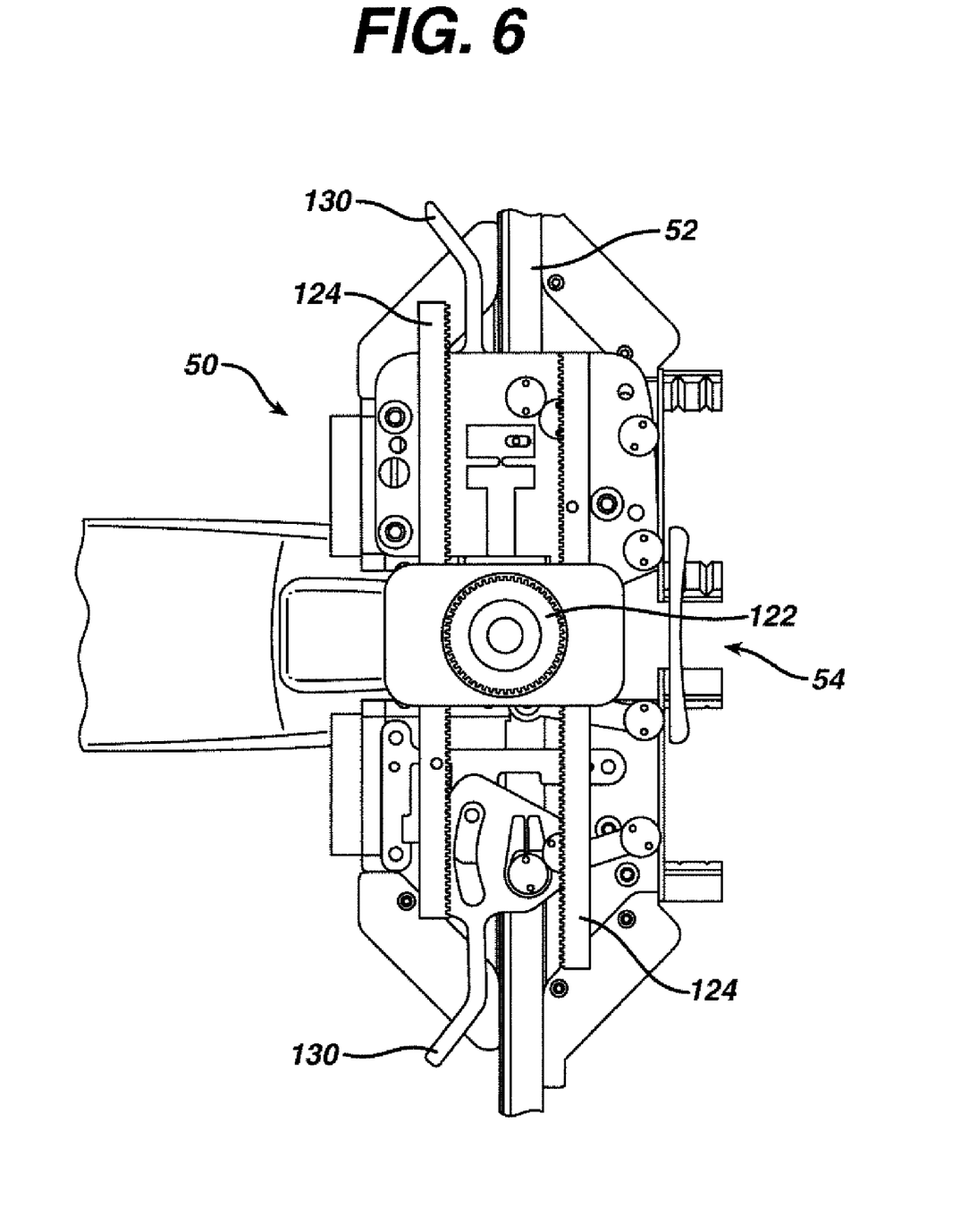
FIG. 6 is a top view of the device of FIG. 5, with portions removed for illustrative clarity.

The illustrated IPD mechanism is connected to a convergence mechanism (discussed below) to provide a variable optical path offset that is capable of keeping the optical path centered on the aperture at various IPD settings during use of the convergence mechanism. The exemplary IPD mechanism is illustrated with greater detail in FIG. 6. As shown in FIGS. 4A, 4B and 6, the mechanism includes a rotatable knob 120 driving a pinion 122 rotatably mounted on the housing 52.

The pinion 122 is disposed between parallel racks 124, and has external teeth meshing with teeth of the racks 124. Each rack 124 supports and/or is fixed to a respective left eye or right eye ocular of the emulator 50. Accordingly, rotating the knob 120/pinion 122 in counterclockwise direction separates the left eye and right eye oculars of the emulator 50, thereby separating the portions to accommodate a greater interpupillary distance, and rotating the knob 120/pinion 122 in a clockwise direction causes the left and right eye oculars of the emulator 50 to approach one another to accommodate a lesser interpupillary distance, as best shown in FIG. 6.

Figure 5:
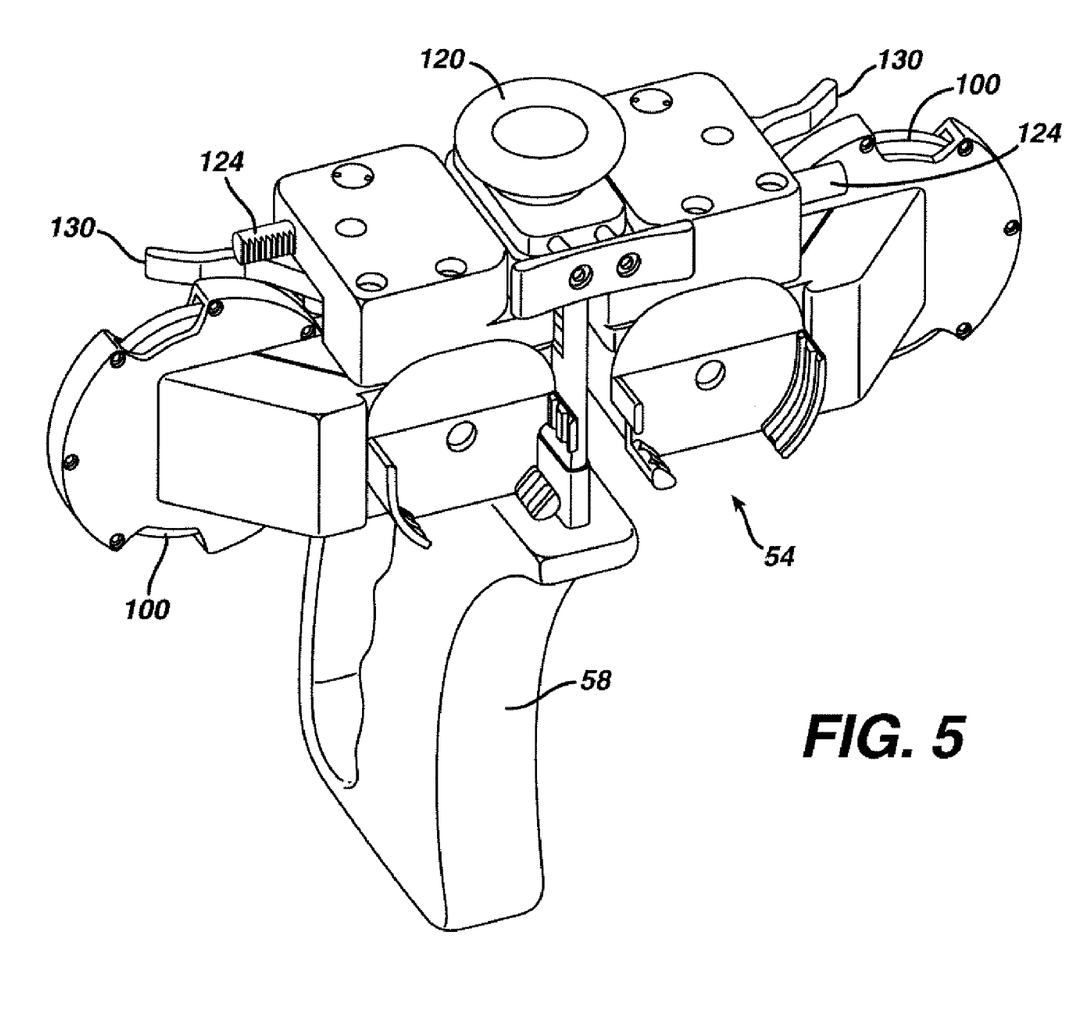
FIG. 5 is a perspective view of an alternative embodiment of the device of FIGS. 4A-4C.

FIG. 5 is a perspective view of an alternative embodiment of the emulator 50 of FIGS. 4A-4C. The oculars and IPD mechanism of the exemplary emulator 50 of FIG. 5 are very similar to those of FIGS. 4A-4C. In addition, each ocular of the emulator 50 of FIG. 5 includes a convergence mechanism capable of pivoting one or both of the left and right oculars of the emulator 50 to cause the left eye and right eye sight paths to intersect at a predetermined reading or near activity distance. Preferably, the oculars pivot about a fixed point located at the nominal center of rotation of the eye sockets when the emulator 50 is held against the face. This convergence mechanism allows a person to focus at a point relatively close to the person's face, e.g. in the range of about 12 to 24 inches from the person's face, to simulate a condition in which a person's eyes pivot in their sockets to focus at a point near the face, e.g. for reading. This allows for testing of visual acuity in a situation simulating reading, which produces a vision prescription for multifocal lenses that will be well-suited to reading or other near vision tasks.

An exemplary convergence mechanism is shown in FIG. 6. As shown in FIG. 6, this convergence mechanism includes first and second levers 130, each of which is pivotably mounted to the housing 52 for movement from a first position in which the left eye and right eye sight paths are substantially parallel (as in FIG. 6), e.g. to simulate a condition in which focusing occurs at a significant distance, e.g. greater than about twenty (20) feet, to a second position in which the left eye and right eye sight paths intersect (as in FIG. 7), e.g. to simulate a reading or similar condition. Generally, this requires pivoting of each ocular in the range of about 7 to 12 degrees for an interpupillary distance in the range of about 55 to 72 mm for focusing at a range of about 14 to 22 inches. Any convergence mechanism capable of pivoting the oculars to cause the left and right eye sight paths to intersect may be used. Preferably, the convergence mechanism causes rotation of the oculars about the nominal center of rotation of the human eyes when the emulator is against the face. The nominal center of rotation of the eyes is approximately 15 mm behind the anterior surface of the cornea.

Figure 7:
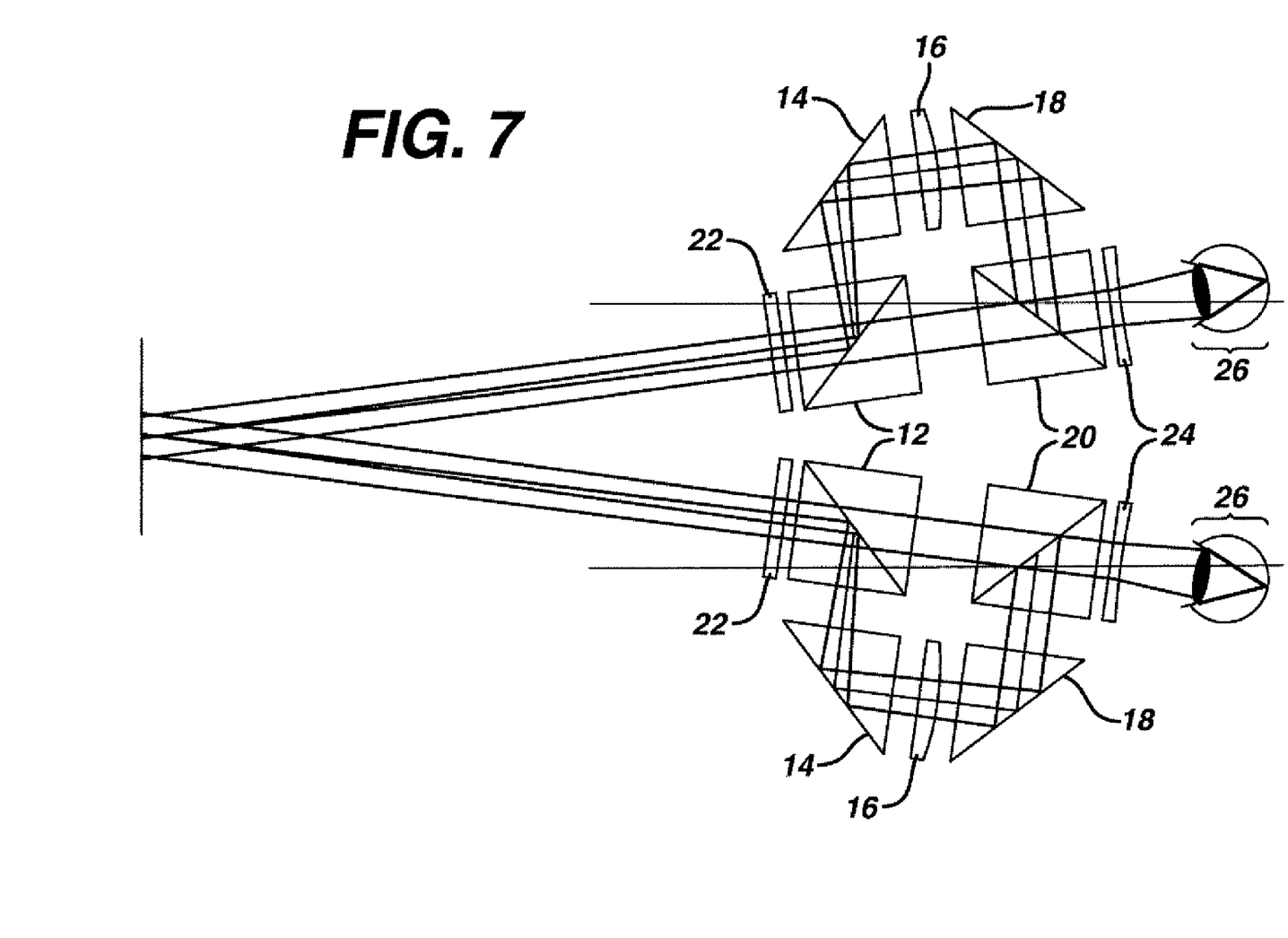
FIG. 7 is a schematic diagram illustrating a convergence feature of the device of FIG. 6.

FIG. 7 is a schematic diagram illustrating the effect of the convergence mechanism of the device of FIGS. 5 and 6. As will be appreciated from FIG. 7, light energy passing through the emulator 50 travels along intersecting sight paths when the left eye and right eye oculars of the emulator 50 are pivoted toward each other to provide the convergence effect.

Figure 8:
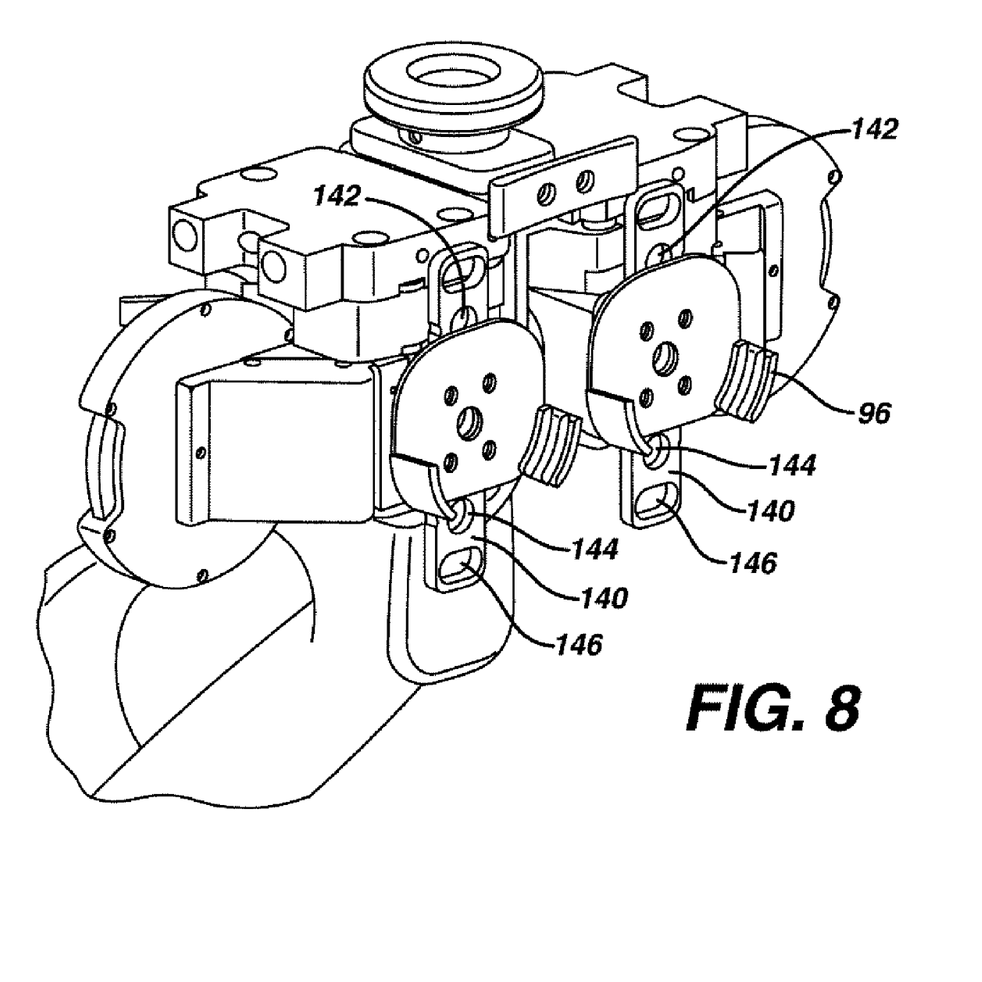
FIG. 8 is a perspective view of another alternative embodiment of the device of FIGS. 4A-4C.

FIG. 8 is a perspective view of another alternative embodiment of the emulator 50 of FIGS. 4A-4C. The oculars and IPD mechanism of the exemplary emulator 50 of FIG. 8 are very similar to those of FIGS. 4A-4C. In addition, each ocular of the emulator 50 of FIG. 8 includes a sphere adjustment member 140 supporting a plurality of sphere lenses 142,144 of various powers. For example, these sphere lenses may collectively provide for power adjustment in quarter diopter increments (e.g.+0.50, +0.25, −0.25, −0.50 diopters). Each sphere adjustment member 140 is movably supported on the housing 52 to allow selective alignment of a selected sphere lens 142,144 with the common optical path for each respective eye portion. Preferably, the sphere adjustment member 140 also includes a lens-free opening 146, or a plano/0.00 diopter lens, selectively alignable with the common optical path. Although the sphere adjustment member 140 may be provided as a rotatable wheel (not shown), it is preferably provided as a longitudinally translatable elongated strip, as shown in FIG. 8.

Accordingly, the sphere lenses of the sphere adjustment members 140 are optically alignable with the oculars and the second and third receptacles and any sphere and/or cylindrical lenses provided therein, with the respective common optical paths. Accordingly, the sphere lenses of the sphere adjustment members 140 may be used to fine tune a vision prescription by first finding an appropriate sphere lens that is positioned in the second receptacle/drop holder 96. For example, such sphere lenses may be provided in 0.50 diopter increments. Then, the sphere adjustment members 140 may be translated to provide adjustments to the total applied sphere power in 0.25 diopter increments. Advantageously, this may be performed without the need to remove the emulator 50 from the person's face, or to disrupt the person's viewing of a chart, which is helpful to the person in comparing visual acuity between two different applied sphere powers. A ball or other type detent mechanism may be provided to facilitate the alignment of the lenses of the sphere adjustment members with the corresponding common optical path.

Figure 9:
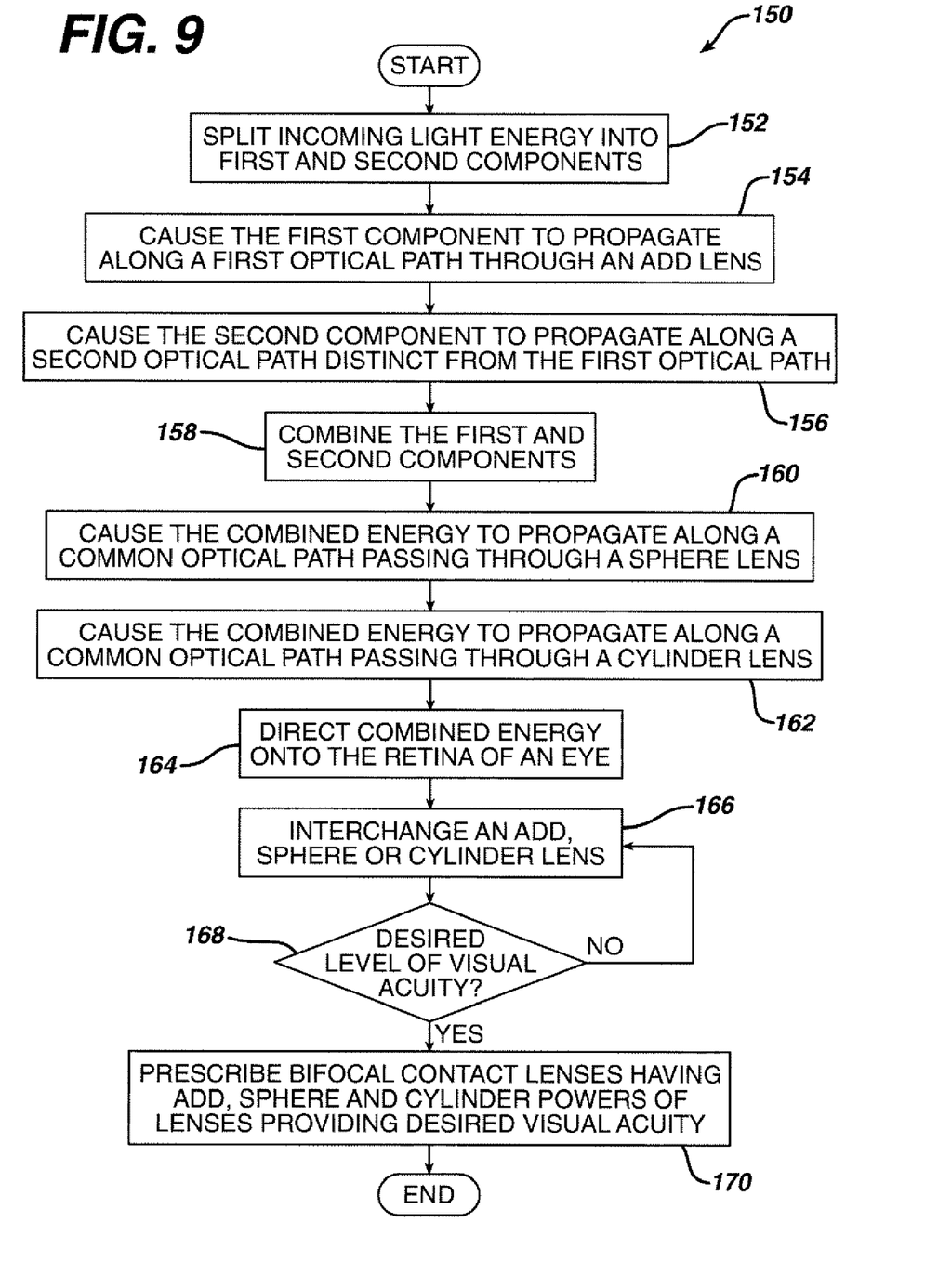
FIG. 9 is a flow diagram illustrating a method for emulating a multifocal contact lens to produce a simultaneous vision effect on a retina of an eye in accordance with the present invention.

FIG. 9 is a flow diagram 150 illustrating a method for emulating a multifocal contact lens to produce a simultaneous vision effect on a retina of an eye in accordance with the present invention. As shown in FIG. 9, the method begins with splitting of incoming light energy into first and second components, as shown at step 152. This involves passing the incoming light energy through the beam splitter 12, and optionally the absorption polarizer 10 to create first and second components having distinct polarizations, as shown in FIG. 1.

Next, the first component is caused to propagate along a first optical path through an add lens, as shown at step 154. The involves directing the first component along a first optical path. This also may be performed by the beam splitter 12. In the example of FIG. 1, this also involves reflecting the light energy of the first component via a reflector 14 through the add lens 16.

Additionally, the beam splitter 12 causes the second component to propagate along a second optical path distinct from the first optical path, as shown at step 156. Accordingly, this results in passing of light energy of only the first component through the add lens.

Next, the first and second components of the light energy are recombined and caused to propagate along a common optical path passing through a sphere lens, as shown at steps 158 and 160. This may involve reflecting the light energy of the first component via a reflector 18 toward a beam combiner 20 (see FIG. 1). The beam combiner combines the components and causes them to travel a common optical path through a sphere lens.

Further, the combined light energy is caused to propagate along a common optical path passing through a cylindrical lens, and is directed onto a retina of an eye, as shown at steps 162 and 164.

Next, the method involves iteratively interchanging at least one of the add, sphere and/or cylindrical lenses until a desired level of visual acuity is provided, as shown at steps 166 and 168. This may involve allowing the person to view the eye chart with a first applied combination of powers/lenses, allowing the person to view the eye chart with a second applied combination of powers/lenses, and taking a report from the person as to which combination provides better visual acuity. This may be repeated until a satisfactory or optimal combination is found. The desired level of acuity may be determined by the person's perception, an objective guideline, applicable laws, etc., as will be appreciated by those skilled in the art.

When the desired level of visual acuity has been reached, a vision prescription may be prepared to reflect the add, sphere and/or cylindrical powers of the combination of lenses providing the desired level of visual acuity, as shown at step 170. Multifocal contact lenses meeting that prescription may then be dispensed to the person with a high degree of confidence that the dispensed multifocal contact lenses will provide the desired level of visual acuity.

Figure 10:
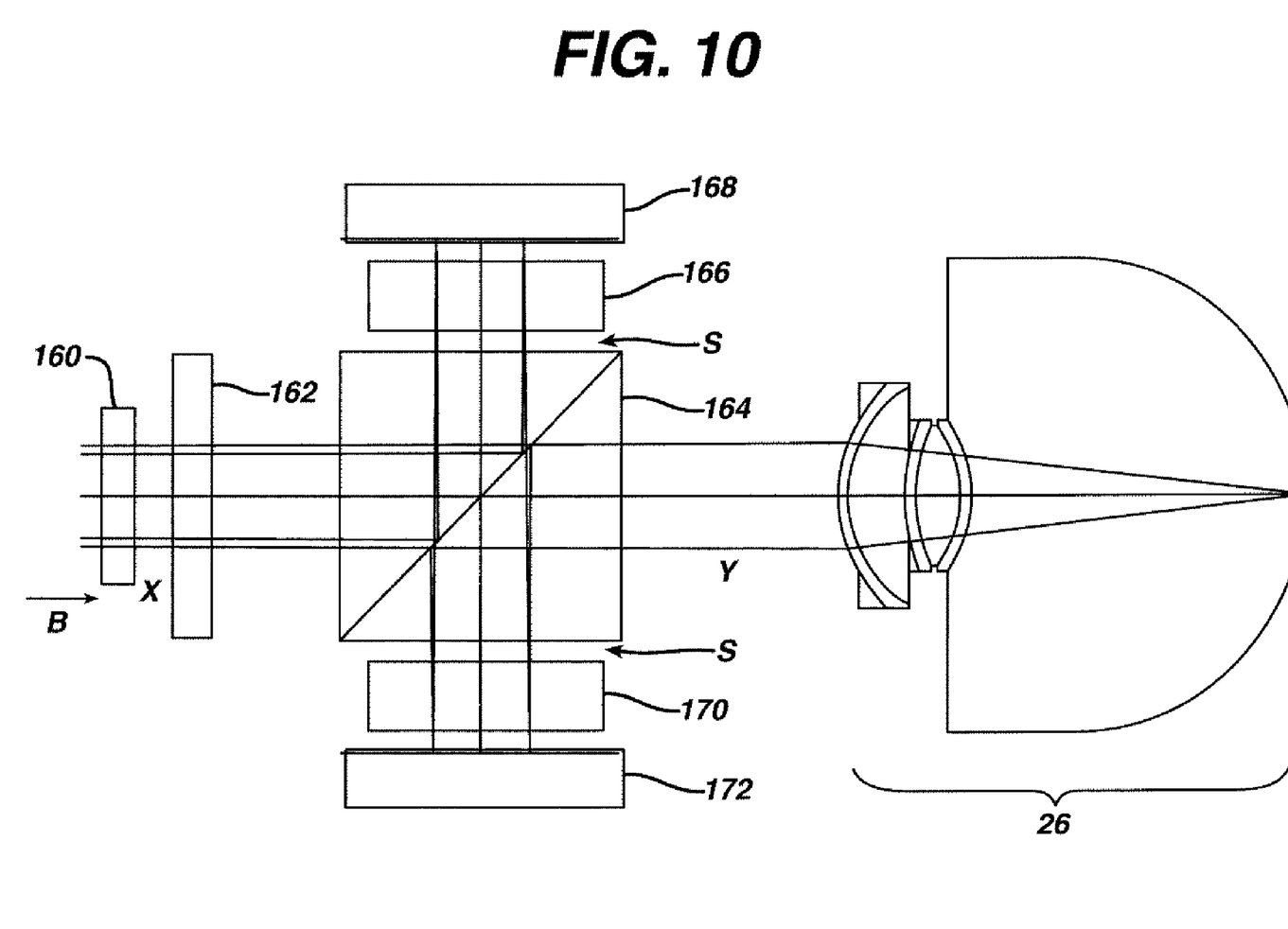
FIG. 10 is a schematic diagram of another simultaneous vision emulator in accordance with the present invention.

FIG. 10 is a schematic diagram of another simultaneous vision emulator 50 in accordance with the present invention. This emulator 50 operates on a similar principle to that discussed with reference to FIGS. 1-9. In the example of FIG. 10, light energy travels in the direction of arrow B and passes through an optional polarizer 160, e.g. a plate absorption polarizer, and a trial frame lens 162 that applies a sphere or "distance" power. As discussed above with reference to FIG. 1, the polarizer 160 can be used to adjust the ratio between components of the incoming light energy that will be directed along the sphere and add paths after passing through the beamsplitter 164. The light energy exiting the trial frame lens 162 enters a visible waveband polarizing beamsplitter 164, which produces first and second light energy components. A first component ("P" polarization) of the light energy goes straight through the beamsplitter 164 and is sphere only in focal length or "power diopters." A second component ("S" polarization) of the light energy is reflected by the beamsplitter 164 through an achromatic quarter waveplate 166 to a mirror 168. The achromatic quarter waveplate 166 is oriented relative to the optical path to rotate "S" polarization to "P" polarization after a double pass through it. The waveplate 166 will also rotate "P" polarization to "S" polarization after a double pass through it. The light energy reflected by the mirror 168 passes back through the achromatic quarter waveplate 166. As a result of the double pass of light energy through the waveplate 166, the light energy reentering the beamsplitter 164 has a "P" polarization. As a result of this polarization, the light energy passes through the beamsplitter 164 and through another achromatic quarter waveplate 170 toward another mirror 172. This second mirror 172 can be changed or deformed to have a concave curvature of a varying amount such that the mirror will act as an add lens to apply an add power.

Light energy reflected from the second mirror 172 then passes back through the second achromatic quarter waveplate 170. This double pass of light energy through waveplate 170 causes the light energy reentering the beamsplitter 164 to have an "S" polarization again. Because the light energy now has an "S" polarization, it is reflected by the beamsplitter 164 towards the eye 26.

It will be appreciated that an achromatic Fresnel rhomb or other component may be substituted for the achromatic quarter waveplate to provide the quarter shift.

Optionally, a slot for a cylindrical trial frame lens (not shown) to match a person's astigmatism may be provided to the left or right of the beamsplitter 164 as shown in FIG. 10. Alternatively, the lens 160 is positioned on the right side of the beamsplitter 164, just before the eye 26. As another alternative, either or both mirrors may be curved as described above to separately or cooperatively apply an add power.

Accordingly, in the embodiment of FIG. 10, like the embodiments of FIGS. 1-8, incoming light energy is split into a first component directed along a first optical path S (involving reflection by the mirrors and passage through the achromatic quarter waveplates), and a second component directed along a second optical path P distinct from the first optical path (involving passage directly through the beamsplitter/polarization cube 164 of FIG. 10). Additionally, this embodiment applies an add power to light energy of only the first component. In this exemplary embodiment, the add power is applied by reflecting the light energy from a curved mirror. Alternatively, an add lens may be used. Furthermore, light energy of the second component, and the first component after the first component has had the add power applied, are directed along a common optical path, namely, toward the retina of the eye.

The combined light energy traveling along the common optical path is also passed through a sphere lens 162. This may occur before or after passage through the beamsplitter 164 (shown before in FIG. 10). Additionally, the combined light energy having the applied add and sphere powers is directed onto the retina of an eye 26 to create the simultaneous vision effect.

Having thus described particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A device for emulating a multifocal contact lens to produce a simultaneous vision effect on a retina of an eye, the device comprising:

a beam splitter positioned to split incoming light energy into a first component directed along a first optical path, and a second component directed along a second optical path distinct from said first optical path;

a first receptacle positioned to pass light energy directed along said first optical path only, said first receptacle being capable of receiving an add lens;

a beam combiner positioned to combine light energy of said second component with light energy of said first component that has passed said first receptacle, and to direct said combined light energy along a common optical path; and a second receptacle positioned to pass the combined light energy traveling along said common optical path, said second receptacle being capable of receiving a sphere lens.

2. The device of claim 1, wherein said beam splitter and said beam combiner each comprise a cube beam splitter.

3. The device of claim 1, wherein said beam splitter and said beam combiner each comprise a cube beam polarizer.

4. The device of claim 1, further comprising:

an absorption polarizer for linearly polarizing incoming light energy.

5. The device of claim 4, wherein said absorption polarizer is rotatably mounted relative to said beam splitter for varying a ratio of intensity between said first and second components produced by said beam splitter.

6. The device of claim 1, further comprising;
a third receptacle positioned to pass combined light energy traveling along said common optical path, said third receptacle being capable of receiving a cylindrical lens.

7. The device of claim 6, wherein said second receptacle is positioned along said common path intermediate said beam combiner and said third receptacle.

8. The device of claim 6, wherein said second and third receptacles each comprise a respective drop lens holder.

9. The device of claim 1, wherein said first receptacle comprises a slot for receiving a lens insert.

10. The device of claim 1, further comprising:
a first reflector for redirecting said first component's light energy from said beam splitter through said first receptacle; and
a second reflector for redirecting said first component's light energy from said first reflector to said beam combiner.

11. The device of claim 10, wherein each of said first and second reflectors comprises a respective total internal reflection prism.

12. The device of claim 1, further comprising:
a wheel capable of supporting a plurality of add lenses each providing a respective add power, said wheel being rotatably mounted relative to said beam splitter for positioning a selected one of said plurality of add lenses in said first receptacle to pass light energy of said first component.

13. The device of claim 1, further comprising:
a sphere adjustment member supporting a plurality of sphere lenses of various powers, said sphere adjustment member being movably supported on said housing for aligning a selected one of said plurality of sphere lenses with said common optical path.

14. The device of claim 13, wherein said sphere adjustment member comprises a longitudinally translatable strip.

15. The device of claim 13, wherein said sphere adjustment member comprises a lens-free opening selectively alignable with said common optical path.

16. The device of claim 13, wherein said plurality of lenses collectively provide for power adjustment in quarter diopter increments.

17. A device for emulating a multifocal contact lens to produce a simultaneous vision effect on a retina of an eye of an individual, the device comprising:
a housing;
a first device according to claim 1 supported on said housing in position to align said common optical path of said first device with a left eye of the individual; and
a second device according to claim 1 supported on said housing in position to align said common optical path of said second device with a right eye of the individual.

18. The device of claim 17, further comprising:
an interpupillary distance mechanism capable of varying the distance between said respective third receptacles to align said respective common paths with pupils of the individual's left and right eyes.

19. The device of claim 17, further comprising:
a convergence mechanism capable of pivoting at least a portion of said first and second devices to cause the respective axes of said respective first receptacles to intersect.

20. The device of claim 17, further comprising:
first and second wheels each supporting a plurality of add lenses providing a respective add power, each of said first and second wheels being rotatable to selectively position a selected one of said plurality of add lenses in a respective first receptacles to pass light energy of a respective first component.

21. The device of claim 17, further comprising:
first and second sphere adjustment members each supporting a plurality of sphere lenses of various powers, each of said first and second sphere adjustment members being movably supported on said housing to selectively align a selected one of a respective one of said plurality of sphere lenses with a respective one of said common optical paths.

22. The device of claim 21, wherein each of said first and second sphere adjustment members comprises a strip longitudinally translatable on said housing with respect to a respective one of said common optical paths.

23. The device of claim 21, wherein each of said first and second sphere adjustment members comprises a lens-free opening selectively alignable with a respective one of said common optical paths.

24. The device of claim 21, wherein said plurality of lenses collectively provide for power adjustment in quarter diopter increments.

* * * * *